US007632514B2

(12) United States Patent
Johannes et al.

(10) Patent No.: US 7,632,514 B2
(45) Date of Patent: Dec. 15, 2009

(54) UNIVERSAL CARRIER FOR TARGETING MOLECULES TO GB3 RECEPTOR EXPRESSING CELLS

(75) Inventors: Ludger Johannes, Courbevoie (FR); Eric Tartour, Paris (FR); Bruno Goud, Paris (FR); Wolf Herve Fridman, Paris (FR)

(73) Assignees: Institute Curie, Paris (FR); Centre National de la Recherche Scientifque, Paris (FR); Institut National de la Sante et de la Recherche Medicale, Paris (FR); Universite Pierre et Marie Curie (Paris VI), Paris (FR)

( * ) Notice: Subject to any disclaimer, the term of this patent is extended or adjusted under 35 U.S.C. 154(b) by 0 days.

(21) Appl. No.: 10/628,415

(22) Filed: Jul. 29, 2003

(65) Prior Publication Data

US 2004/0110935 A1 Jun. 10, 2004

Related U.S. Application Data

(63) Continuation of application No. PCT/EP02/01627, filed on Feb. 1, 2002.

(30) Foreign Application Priority Data

Feb. 1, 2001 (EP) .................................. 01400255

(51) Int. Cl.
| | |
|---|---|
| *A61K 39/38* | (2006.01) |
| *A61K 39/00* | (2006.01) |
| *A61K 39/02* | (2006.01) |
| *A61K 39/385* | (2006.01) |
| *C07K 2/00* | (2006.01) |
| *C07K 4/00* | (2006.01) |
| *C07K 5/00* | (2006.01) |
| *C07K 7/00* | (2006.01) |
| *C07K 14/00* | (2006.01) |
| *C07K 17/00* | (2006.01) |
| *C07K 16/00* | (2006.01) |

(52) U.S. Cl. .............. 424/236.1; 424/184.1; 424/185.1; 424/190.1; 424/193.1; 424/234.1; 530/300; 530/324; 530/350

(58) Field of Classification Search ................. 530/300, 530/350, 324; 424/184.1, 236.1
See application file for complete search history.

(56) References Cited

U.S. PATENT DOCUMENTS

| 4,810,643 | A | | 3/1989 | Souza | |
|---|---|---|---|---|---|
| 5,994,311 | A | * | 11/1999 | Eichner et al. ................. | 514/18 |
| 6,613,882 | B1 | | 9/2003 | Goud et al. .................. | 530/350 |
| 6,652,857 | B2 | * | 11/2003 | Williams et al. .......... | 424/169.1 |
| 6,777,202 | B2 | * | 8/2004 | Lubitz et al. ................ | 435/69.1 |
| 6,855,321 | B1 | * | 2/2005 | Rappuoli et al. .......... | 424/192.1 |
| 7,488,809 | B2 | * | 2/2009 | Goud et al. .................. | 530/402 |
| 2004/0047883 | A1 | * | 3/2004 | Goud et al. .............. | 424/236.1 |
| 2004/0110935 | A1 | * | 6/2004 | Johannes et al. ............ | 530/395 |
| 2006/0008475 | A1 | * | 1/2006 | Johannes et al. ......... | 424/249.1 |
| 2009/0035330 | A1 | * | 2/2009 | Dewerchin ............... | 424/241.1 |
| 2009/0092578 | A1 | * | 4/2009 | Su et al. .................... | 424/85.2 |

FOREIGN PATENT DOCUMENTS

| EP | 2766193 | A1 | * | 1/1999 |
|---|---|---|---|---|
| EP | 1229045 | A1 | * | 8/2002 |
| EP | 1386927 | A1 | * | 2/2004 |
| WO | WO 95/11998 | A1 | * | 5/1995 |
| WO | WO 99/03881 | A2 | | 1/1999 |
| WO | WO 02/060937 | A1 | | 8/2002 |
| WO | WO 2004/016148 | A2 | * | 2/2004 |

OTHER PUBLICATIONS

Kim et al, Abstracts of the Interscience Conference on Antimicrobial Agents and Chemotherapy, 2003, 43:294 Abstract.*
Ling et al, Biochemistry, 1998, 37:1777-1788.*
Su et al, Infection and Immunity, 1992, 60/8:3345-3359.*
Sandvig, Toxicon, 2001, 39:1629-1635.*
Schoen et al, International J. Medical Microbiology, 2004, 294:319-335.*
Xu et al, Vaccine, 2003, 21:644-648.*
Tzschaschel et al, Microbial Pathogenesis, 1996, 21:277-288.*
Bast t al, Molecular Microbiology, 1999,32/5:953-960.*
Dubos et al, J. Exp. Med., 1946, 56:143-156.*
O'Loughlin et al, Microbes and Infection, 2001, 3:493-507.*
Herold et al, International J. Medical Microbiology, 2004, 294:115-121.*
Makino et al, Microbial Pathog nesis, 2001, 31:1-8.*
Sandvig et al, FEBS Letters, 2002, 529:49-53.*
Ohmura-Hoshino et al, Vaccine, 2004, 22:3751-3761.*
Tarrago-Trani et al, Protein Expression and Purification, 2004, 38:170-176.*
Hagn r Ile et al, J. Structural Biology, 2002, 139:113-121.*
Pruimboom-Brees et al, PNAS,USA, 2000, 97/19:10325-10329.*
Rapak et al, PNAS, USA, Apr. 1997, 94:3783-3788.*
Mallard et al, JCB, Nov. 16, 1998, 143/4:973-990.*

(Continued)

*Primary Examiner*—Nita M Minnifield
(74) *Attorney, Agent, or Firm*—Birch, Stewart, Kolasch & Birch, LLP

(57) ABSTRACT

The present invention concerns an universal polypeptidic carrier for targeting directly or indirectly a molecule to Gb3 receptor expressing cells and having the following formula STxB-Z(n)-Cys, wherein: STxB is the Shiga Toxin B subunit or a functional equivalent thereof, Z is an amino-acid devoided of sulfydryl group, n being 0, 1 or a polypeptide, Cys is the amino-acid Cysteine, and the use thereof for MHC class I and MHC class II presentation of antigens.

11 Claims, 10 Drawing Sheets

OTHER PUBLICATIONS

Johann s et al, JBC, Aug. 1, 1997, 272/31:19554-19561.*
Ryd et al, Microbial Pathogenesis, 1992, 12:399-407.*
Waldrep, Drugs of Today, 1998, 34/6:549-561.*
Calderwood et al, PNAS,USA, Jul. 1987, 84:4364-4368.*
Sandvig et al, Nature, Aug. 1992, 358:510-512.*
Seidah et al, JBC, Oct. 25, 1986, 261/30:13928-13931.*
Sandvig et al, JCB, Jul., 1994, 126/1:53-64.*
Jones et al, Immunology Letters, Dec. 1990, 26/3:285-290.*
Gaidamakova et al, J. Controlled Release, 2001, 74/1-3:341-347.*
Ling et al, Structure, 2000, 8:253-264.*
Gariepy, Critical Reviews in Oncology/Hematology, 2001, 39:99-106.*
Vingert et al, Eur. J. Immunol., 2006, 36:1124-1135.*
Su et al, Microbial Pathogenesis, Dec. 1992, 13/6:465-476 absctract only.*
Su et al, Infection and Immunity, Aug. 1992, 60/8:3345-3359 abstract only.*
Perera et al, J. Bacteriology, Feb. 1991, 173/3:1151-1160.*
Tarrago-Trani et al, Photochemistry and Photobiology, 2006, 82:527-537.*
Shigematsu et al., Journal of Biotechnology, vol. 75, pp. 23-31 (1999).
Schelte et al., Bioconjugate Chem, vol. 11, pp. 118-123 (2000).
Noakes et al., FEBS Letters, vol. 453, pp. 95-99 (1999).
Haicheur et al., The Journal of Immunology, pp. 3301-3308 (2000).
Lee et al., Eur. J. Immunol., vol. 28, pp. 2726-2737 (1998).
Bao-Yuan Lu et al., Biochemistry, vol. 44 (45), pp. 15032-15041 (2005).
Bartkowski, Richard et al., Journal of Protein Chemistry, vol. 21, No. 3, pp. 137-143 (2002).
Masaharu Ishikawa et al., Cell Structure and Function, vol. 17, pp. 61-65 (1992).

* cited by examiner

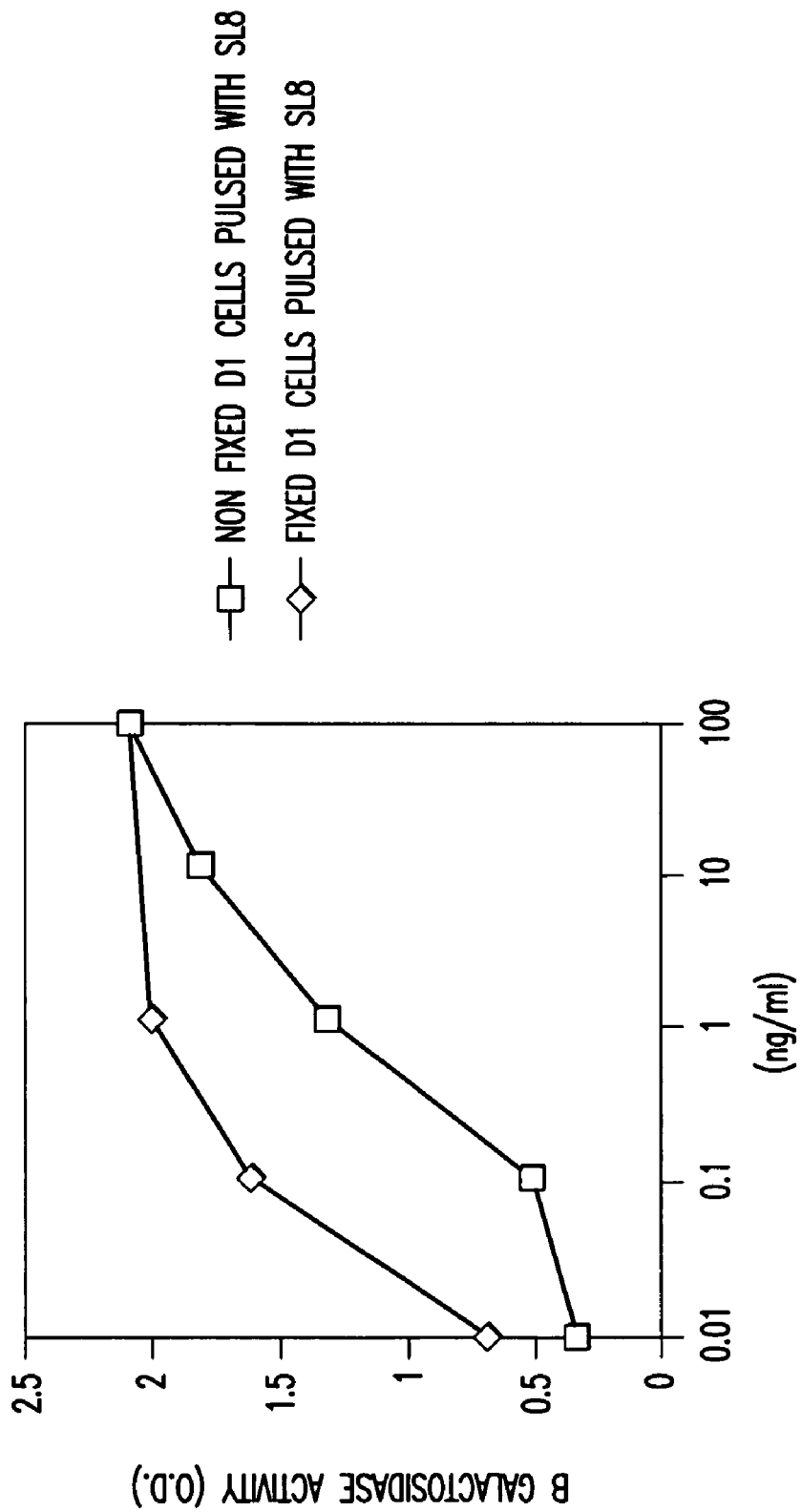

NHS-ESTER REACTION SCHEME

MALEIMIDE REACTION SCHEME

MBS
m-MALEIMIDOBENZOYL-N-HYDROXYSUCCINIMIDE ESTER

SEQUENCE LISTING

<160> NUMBER OF SEQ ID NOS: 7

<210> SEQ ID NO 1
<211> LENGTH: 90
<212> TYPE: PRT
<213> ORGANISM: Artificial Sequence
<220> FEATURE:
<223> OTHER INFORMATION: Description of Artificial Sequence: Universal
      carrier

<400> SEQUENCE: 1

Met Lys Lys Thr Leu Leu Ile Ala Ala Ser Leu Ser Phe Phe Ser Ala
 1               5                   10                  15

```
Ser Ala Leu Ala Thr Pro Asp Cys Val Thr Gly Lys Val Glu Tyr Thr
            20                  25                  30

Lys Tyr Asn Asp Asp Asp Thr Phe Thr Val Lys Val Gly Asp Lys Glu
        35                  40                  45

Leu Phe Thr Asn Arg Trp Asn Leu Gln Ser Leu Leu Leu Ser Ala Gln
    50                  55                  60

Ile Thr Gly Met Thr Val Thr Ile Lys Thr Asn Ala Cys His Asn Gly
65                  70                  75                  80

Gly Gly Phe Ser Glu Val Ile Phe Arg Cys
                85                  90

<210> SEQ ID NO 2
<211> LENGTH: 270
<212> TYPE: DNA
<213> ORGANISM: Artificial Sequence
<220> FEATURE:
<223> OTHER INFORMATION: Description of Artificial Sequence:
                       Polynucleotide

<400> SEQUENCE: 2
atgaaaaaaa cattattaat agctgcatcg ctttcatttt tttcagcaag tgcgctggcg    60
acgcctgatt gtgtaactgg aaaggtggag tatacaaaat ataatgatga cgataccttt   120
acagttaaag tgggtgataa agaattattt ccaacagatg gaatcttca gtctcttctt    180 ctcagtgcgc aaattacggg gatgactgta accattaaaa ctaatgcctg tcataatgga   240
gggggattca gcgaagttat ttttcgttgt                                    270

<210> SEQ ID NO 3
<211> LENGTH: 37
<212> TYPE: DNA
<213> ORGANISM: Artificial Sequence
<220> FEATURE:
<223> OTHER INFORMATION: Description of Artificial Sequence: Primer A

<400> SEQUENCE: 3
agcgaagtta tttttcgttg ttgactcaga atagctc                             37

<210> SEQ ID NO 4
<211> LENGTH: 33
<212> TYPE: DNA
<213> ORGANISM: Artificial Sequence
<220> FEATURE:
<223> OTHER INFORMATION: Description of Artificial Sequence:  Primer B

<400> SEQUENCE: 4
gagctattct gagtcaacac gaaaaataac ttc                                 33

<210> SEQ ID NO 5
<211> LENGTH: 17
<212> TYPE: DNA
<213> ORGANISM: Artificial Sequence
<220> FEATURE:
<223> OTHER INFORMATION: Description of Artificial Sequence: Primer A'
<220> FEATURE:
<221> NAME/KEY: misc_feature
<222> LOCATION: (1)..(17)
<223> OTHER INFORMATION: Primer ShigaAtpE

<400> SEQUENCE: 5
cactactacg tttaac                                                   17

<210> SEQ ID NO 6
```

-continued

```
<211> LENGTH: 15
<212> TYPE: DNA
<213> ORGANISM: Artificial Sequence
<220> FEATURE:
<223> OTHER INFORMATION: Description of Artificial Sequence: Primer B'
<220> FEATURE:
<221> NAME/KEY: misc_feature
<222> LOCATION: (1)..(15)
<223> OTHER INFORMATION: Primer Shiga-fd

<400> SEQUENCE: 6
cggcgcaact atcgg                                                           15

<210> SEQ ID NO 7
<211> LENGTH: 36
<212> TYPE: PRT
<213> ORGANISM: Artificial Sequence
<220> FEATURE:
<223> OTHER INFORMATION: synthetic peptide derived from chicken
                        ovalbumin

<400> SEQUENCE: 7

Leu Glu Gln Leu Glu Ser Ile Ile Asn Phe Glu Lys Leu Thr Glu Trp
1               5                   10                  15

Ser Leu Lys Ile Ser Gln Ala Val His Ala Ala His Ala Glu Ile Asn
            20                  25                  30

Glu Ala Gly Arg
            35
```

UNIVERSAL CARRIER FOR TARGETING MOLECULES TO GB3 RECEPTOR EXPRESSING CELLS

This application is a Continuation of copending PCT International Application No. PCT/EP02/01627 filed on Feb. 1, 2002, which was published in English and which designated the United States and on which priority is claimed under 35 U.S.C. § 120, the entire contents of which are hereby incorporated by reference.

The invention relates to a universal polypeptidic carrier for targeting molecules to a Gb3 receptor for the B-subunit of Shiga-Toxin expressing cells and its use for intracellular transport and processing of said molecules.

Shiga Toxin is a bacterial toxin of the $AB_5$ subunit family that is secreted by *Shigella dysenteriae*. The A-subunit is the toxic moiety and inhibits the protein synthesis in higher eucaryotic target cells after transfering into the cytoplasm of said cells. The B-subunit is an homopentamer protein (5B-fragments) and is responsible for toxin binding to and internalization into target cells by interacting with the glycolipid Gb3 found on the plasma membranes of these cells. The B-fragment is non toxic, but conserves the intracellular transport characteristics of the holotoxin which, in many Gb3 expressing cells, is transported in a retrograde fashion from the plasma membranes to cytosol, via endosomes.

The glycolipid Gb3 receptor has also been reported to be expressed preferentially in some ectodermic derived tumors (plasma) and some Burkitt's lymphoma. It is also known as CD 77. In the present text, the term Gb3 should be considered as an equivalent to CD77.

The authors have already shown that a CD8 human tumor Antigen fused to the B subunit of Shiga toxin could efficiently be presented in an HLA class 1-restricted manner to specific CTL (1). This result was independently confirmed by another study that demonstrated that Shiga holotoxin, carrying a defined peptide epitope from influenza virus, could deliver the antigen into the MHC class I intracellular pathway (3).

The authors have also shown that fusion proteins between the Gb3 receptor-binding non toxic B-fragment of bacterial Shiga toxin derived from *Shigella dysenteriae* and an antigen, or an epitope from a model tumor antigen, can elicit specific cytotoxic T lymphocytes response (CTL), whereas each moiety of said fusion protein does not lead individually to CTL induction (1, 2, and WO 99/03881).

The difficulty of this technology is that, for each application, i.e., for each antigen or fragment thereof, there is a need for a specific construction of a fusion protein, that necessitates a specific construction of a recombinant vector bearing the sequences encoding this fusion protein to be expressed in a host cell.

The aim of the present invention is to overcome the above-mentioned drawbacks and to provide a universal hook, or a universal carrier for targeting a molecule to a Gb3 receptor expressing cell to enable this molecule to be internalized, processed and/or expressed in said cell expressing Gb3 receptor.

In the present invention, a Shiga toxin B-subunit (STxB) derivative, or mutant, termed STxB-Cys has been designed. In this protein, a Cysteine is added at the C-terminus of mature STxB. The protein, when purified from bacteria, carries the internal disulfide bond, as wild type STxB, while the sulfhydryl group at the C-terminal Cys is free. Due to their nucleophilicity, free sulfhydryl groups are excellent acceptors for directed coupling approaches (4).

Thus, the present invention relates to a universal polypeptidic carrier for targeting directly or indirectly a molecule of interest to Gb3 receptor expressing cells having the following formula: STxB-Z(n)-Cys, wherein:

STxB is the Shiga Toxin B subunit or a functional equivalent thereof,

Z is an amino-acid devoided of sulfydryl group, n being 0, 1 or an amino-acid sequence, Cys being the amino-acid Cysteine.

The STxB moiety of the universal carrier has the sequence described in (8) or a functional equivalent thereof. A functional equivalent means a polypeptidic sequence having the capacity to bind specifically to the Gb3 receptor and/or to trigger an internalization of an antigen and its presentation in an MHC class-I restricted pathway, or both MHC class I and class II on the same antigen presenting cell.

In the light of the heterogeneity of expression of tumor antigens, the allele-specific loss of MHC class I expression at the surface of tumor cells, and the necessity to have concomitant presentation of antigens by both MHC class I and class II on the same antigen presenting cell, it is advantageous to couple full size antigen proteins to the B-subunit for targeting to dendritic cells.

In a preferred embodiment, n is 0 and the universal carrier has the following sequence (SEQ ID No 1):

```
COOH - MKKTLLIAASLSFFSASALATPDCVTGKVE
YTKYNDDDTFTVKVGDKELF
TNRWNLQSLLLSAQITGMTVTIKTNACHNGGGFSEVIFRC - NH2
```

As a matter of fact, if the Z linker is too long, i.e., when n is equal or greater than 2, some internal disulfide bridges might occur, and prevent either the binding of STxB to the Gb3 receptor and especially prevent the binding to the molecule of interest.

According to the invention, the molecule of interest is selected in the group constituted of proteins, peptides, oligopeptides, glycoproteins, glycopeptides, nucleic acids, polynucleotides, or a combination thereof.

In another aspect of the invention, the molecule of interest is an antigen to be targeted to antigen presentating cells. Such cells are selected in a group comprising T lymphocytes, dendritic cells, macrophages Langerhans cells and the like.

In another aspect of the invention, the molecule of interest are drugs such as haptenes, psoralenes, or any compounds provided that they have a chemical group linkable with the —SH group of the Cysteine moiety of STxB-Cys.

The drug might be linked either directly or after activation with coumpounds such as bromoacetate, or any other method known by a skilled person, provided that the result of the reaction is a chemical entity having the following formula: STxB-Cys-M, M being all the above mentioned molecules of interest.

The coupling approaches for covalent binding of a peptidic or a polypeptidic moiety to STxB-Z(n)-Cys can be any method or processes described or carried out by a skilled person.

A first method that can be embodied is the use of SPDP hetero-bi-functional cross-linker described par Carlsson et al (5). However, SPDP is capable of being cleavable by serum thiolases that is a cause of decreasing the yield of the reaction.

A second method for covalent coupling of STxB-Z(n)-Cys peptides with another peptide of interest is to produce bromoacetyl or maleimide functions on the latter as described by P. Schelte et al (4). Briefly, the peptide of interest is chemically activated with bromoacetate anhydride or by a maleimide group respectively. In appropriate reaction conditions (pH, temperature, incubation times), these groups are eliminated by cis-elimination, yielding respectively to —S—S, —S—CH$_2$—, to —S—CO— or to —S—NH— covalents linkages.

As an example, the polypeptide or the peptide to be coupled to the —SH moiety the C-terminal Cysteine of the universal carrier, has its N-terminus activated with bromoacetic anhydride following the reaction scheme:

Br—CH$_2$—CO—O—CO—CH$_2$—Br + NH$_2$-peptide ⟹
    Br—CH$_2$—CO—NH-peptide + Br—CH$_2$—COOH The Bromoacetyl function has high chemoselectivity for peptide thiol groups and the activated peptide can be reacted with STxB-Cys as follows:

STxB-Cys-SH+Br—CH$_2$—CO—NH-peptide ⟹ STxB-Cys-S—CH$_2$—CO—NH-peptide+HBr

The resulting thioether-linkage is stable to hydrolysis.

Another method for coupling a molecule to the universal carrier of the invention is to use MBS (m-Maleimidobenzoyl-N-hydroxysuccinimide ester) as shown in FIG. 6 and explained in example 5. This coupling allows the transport and processing of large molecules such antigenic proteins or glycoproteins through MHC class I and/or MHC class II pathways.

Thus, another aspect of the invention is the product resulting from a covalent binding of STxB-Z(n)-Cys with a molecule of interest by a —S—S—, —S—CO—, or S—CH$_2$— or —S—NH— linkage.

In one embodiment, the molecule of interest to be targeted to an antigen presentating cells is constituted by or comprises a polypeptidic structure, such an antigens or epitopes thereof, glycopeptides or glycoproteins, lipopeptides or lipoproteins.

In a preferred embodiment, the product resulting from the coupling of STxB-Z(n)-Cys with an antigen or a fragment thereof, where (n) is 0, 1, or 2, and preferably 0, is able to be presented in an MHC class I and MHC class II restricted pathway.

In another embodiment, the molecule of interest is a polypeptide capable of binding with polynucleotide structures such as DNA or RNA molecules. Such molecules might be vectors or plasmids comprising a sequence of interest to be expressed in a target cell. In the present invention, a target cell is a eucaryotic cell bearing on its membrane the Gb3 receptor.

Thus, the universal carrier of the present invention is also a carrier for introducing a nucleotide sequence in a target cell either for gene therapy or for obtaining recombinant cells expressing heterologous proteins.

In another embodiment, the universal carrier according to the present invention can be operably linked directly through a covalent binding or indirectly through a linker to a cytotoxic drug to be targeted to tumor cells expressing Gb3 receptor.

The term "indirect binding" means that the universal carrier is covalently linked through the sulfhydryl moiety of the C-terminal Cysteine to a linker, said linker being operably linked to a drug or a pro-drug to be internalized into Gb3 receptor bearing cells.

This linkage might be a covalent binding or a non-covalent binding, provided that the affinity between the linker and the drug (or the pro-drug) is higher than $10^{-9}$ mole/l.

Another aspect of the invention is an isolated polynucleotide selected from the group of:

(a) a polynucleotide comprising the nucleotide sequence STxB encoding the Shiga Toxin B subunit or a functional equivalent thereof bearing at its 3'end the codon TGT, or the codon TGC encoding Cysteine;

b) a polynucleotide comprising a nucleotide sequence having at least 80% sequence identity to a nucleotide sequence encoding the Shiga Toxin B subunit or a functional equivalent thereof bearing at its 3'end the codon TGT or TGC; and c) a nucleotide sequence complementary to the sequence in a) or b).

In a preferred embodiment, the polynucleotide has the following SEQ ID NO: 2:

```
5'-atgaaaaaaacattattaatagctgcatcgctttcattttttcagc
aagtgcgctggcgacgcctgattgtgtaactggaaaggtggagtatacaa
aatataatgatgacgatacctttacagttaaagtgggtgataaagaatta
tttaccaacagatggaatcttcagtctcttcttcttcagtgcgcaattac
ggggatgactgtaaccattaaaactaatgcctgtcataatggagggggat
tcagcgaagttattttcgttgt-3'
```

The present invention relates also to a recombinant vector or to a plasmid comprising a polynucleotide sequence as described above, and capable of expressing the universal carrier STxB-Z(n)-Cys, where (n) is 0, 1 or 2, STxB and Z have the same significance as above, in an appropriate host cell.

As an example, a convenient vector is the plasmid pSu108 described in (7).

Another object of the present invention is to provide a method for obtaining a plasmid expressing STxB-Z(n)-Cys comprising:

a) providing a plasmid comprising a STxB sequence;
b) applying two PCR amplification steps using two couples of primers, AA' and BB',
   A and B being complementary to each other and comprising the Cys codon,
   A' and B' being outside the STxB sequence;
c) isolating the amplified fragments;
d) hybridizing the amplified fragments;
e) applying a PCR amplification on the hybridized fragments;
f) insertion of the amplified fragment into a plasmid.

In a preferred embodiment, the plasmid pSU108 (7) containing STxB fragment was modified to introduce the Cysteine codon TGT at the 3' end of the B-fragment cDNA. The primers for step b) are respectively for AA' and BB':

```
primer A:                           (SEQ ID NO: 3)
5'-AGCGAAGTTATTTTTCGTTGTTGACTCAGAATAGCTC-3', and primer B:                           (SEQ ID NO: 4)
5'-GAGCTATTCTGAGTCAACACGAAAAATAACTTC-3'.

primer A':                          (SEQ ID no 5)
primer ShigaAtpE "5'-CACTACTACGTTTTAAC-3', and, primer B':                          (SEQ ID NO: 6)
primer Shiga-fd: 5'-CGGCGCAACTATCGG-3'.
```

The PCR of step e) yields a fragment that is cloned into the SphI and SalI restriction sites of pSU108. Sequences derived by PCR are verified by dideoxy-sequencing.

The skilled person can easily design the choice of primers, plasmids for producing a vector bearing the polynucleotide sequence expressing STxB-Z(n)-Cys in an appropriate host cell, provided that this succession of steps allows the interpretation of the Cys codon into the amplified fragment.

The invention also provides a recombinant cell line obtained by transformation with the recombinant vector containing the polypeptide sequence encoding the universal carrier as described above. In a preferred embodiment, said recombinant cell line is a procaryotic cell, preferentially *E. coli*.

In a still preferred embodiment, the plasmid is pSU108 having SEQ ID No. 2 integrated between the SphI and SalI restriction sites, and the corresponding cell line has been deposited at CNCM on Dec. 19, 2000 with the registration number 1-2604.

The present invention also provides a process for producing a universal carrier as described above comprising:
a) culturing a recombinant cell line as described above,
b) obtaining a periplasmic extract of said cells, and
c) purifying said polypeptide.

Preferentially, the cell line is *E. coli* and in c) the purification is made by anion exchange column chromatography followed by a gel filtration column chromatography.

Such a process is particularly advantageous for large scale production of the universal carrier, as far as it can then be operably linked by covalent coupling with a molecule of interest, and used within a large scope of application.

The present invention also provides a method for delivering a sequence of interest into the MHC class I pathway using a product obtained by covalent binding of the Cys moiety of the universal carrier with said sequence of interest; this method is advantageous to elicit a CTL response to a given antigen or epitope thereof as far as the product is specific to the cell involved in the MHC class I pathway.

As a matter of fact, the inventors have shown that an immunodominant peptide, derived from the ovalbumin protein, and coupled chemically to STxB-Cys, could be presented by antigen presenting cells to specific hybridoma cells, demonstrating that STxB could deliver exogenous immunogenic peptide in the MHC class I pathway. To exclude a bias due to the presence of free peptides contaminating the material, experiments using fixed dendritic cells clearly demonstrated that the internalization of the fusion protein was required for this process. The inventors also have shown that the Shiga toxin receptor, $Gb_3$, was also involved in the ability of STxB-Cys to target exogenous peptide in the endogenous MHC class I pathway.

The invention also pertains to a method for delivering an expression vector containing a sequence of interest into a Gb3 receptor expressing cells characterized in that said expression vector is bound to a lysine rich peptide covalently linked to the Cys moiety of the universal carrier.

As an example, the lysine rich peptide is a 16-mer polylysine which is able to bind any polynucleotidic sequence, either of DNA or RNA nature. Such a peptide carrying a 16-mer of lysines will be activated at its N-terminus by bromoacetate anhydride and coupled to STxB-Cys. Expression plasmids will be bound to this coupling product, and vectorization of DNA into target cells is assayed using convenient reporter systems, such as the green fluorescent protein or luciferase.

The capacity to target expression plasmids with the help of STxB to the nucleus of antigen presenting cells is expected to further improve the power of this vector, since i) DNA can even more easily be adopted to new experimental or clinical needs, and ii) due to its potentiation effect, expression of antigenic peptides or proteins from DNA would further increase the sensitivity of STxB-dependent antigen presentation.

The invention also provides a method for delivering a drug or a pro-drug into a cell, particularly into a cancer cell bearing Gb3 (or CD77) receptor.

The glycolipid $Gb_3$ receptor has been reported to be preferentially expressed in some neuroectodermic derived tumors (glioma) and some Burkift's lymphoma. Since one limitation of the use of chemotherapy in cancer is secondary side effects of the drugs because of their toxicity on normal cells, the drugs are preferentially vectorized in tumor cells by using STxB-Cys. The drugs are activated to become reactive with the sulfhydryl group of STxB-Cys. To achieve this, a maleimide group can be introduced on a drug, for example psoralenes compounds.

The present invention also pertains to:
a pharmaceutical composition for enhancing the immunogenicity of a peptide or a protein or a glycoprotein or a lipopeptide, containing the universal carrier covalently linked by its Cys moiety to said peptide or protein or glycoprotein or lipopeptide;
a pharmaceutical composition for treating tumor cells bearing the Gb3 receptor (CD77), containing the universal carrier according to the invention covalently linked by its Cys moiety to a drug or a pro-drug toxic for said tumor cells.

Without limiting the scope of the universal carrier of the invention and its widespread use in different applications, the hereinafter examples and figures illustrate the advantages of the present invention.

LEGEND OF THE FIGURES

FIG. 1 represents the protein profile of the final SephaDex 75 column yielding purified STxB-Cys. Fractions 20-25 contain mostly monomeric STxB-Cys (the positions of monomeric and dimeric STxB-Cys are indicated to the right). Molecular weight markers are indicated to the left.

FIG. 2*a* represents the coupling of Type2 of Pep2 [as defined in example 2] to STxB-Cys, followed by an in vitro antigen presentation assay on D1 dendritic cells, as described in (2). Two different preparations of STxB-Cys coupled to the SL8 peptide, an immunodominant epitope of ovalbumin were used (termed 4A and 9A). Upon fixation, antigen presentation is abolished showing that no extracellular processing occured.

FIG. 2*b* represents a control experiment of FIG. 2*a*, in which it is shown that fixed D1 can still present free SL8 peptide.

Figure 6:
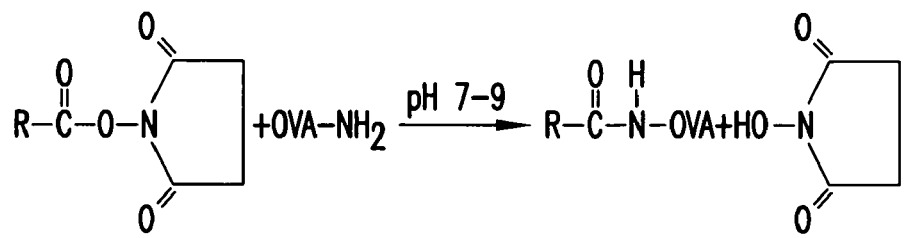
Figure 6:
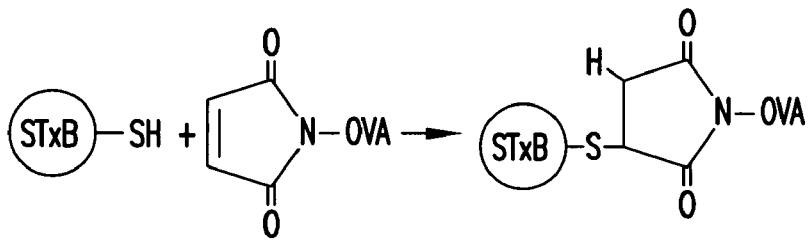
Figure 6:
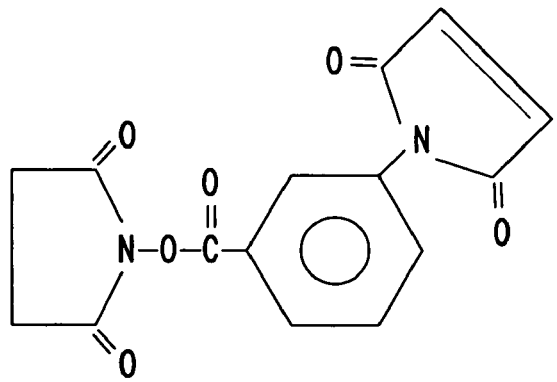

FIG. 6 represents reaction scheme for full size Ova coupling to STxB-Cys using the heterobifunctional cross linker MBS. Top: first reaction linking MBS to primary amines of Ova. Middle: second reaction between activated Ova and STxB-Cys. Bottom: Structure of MBS.

Figure 7:
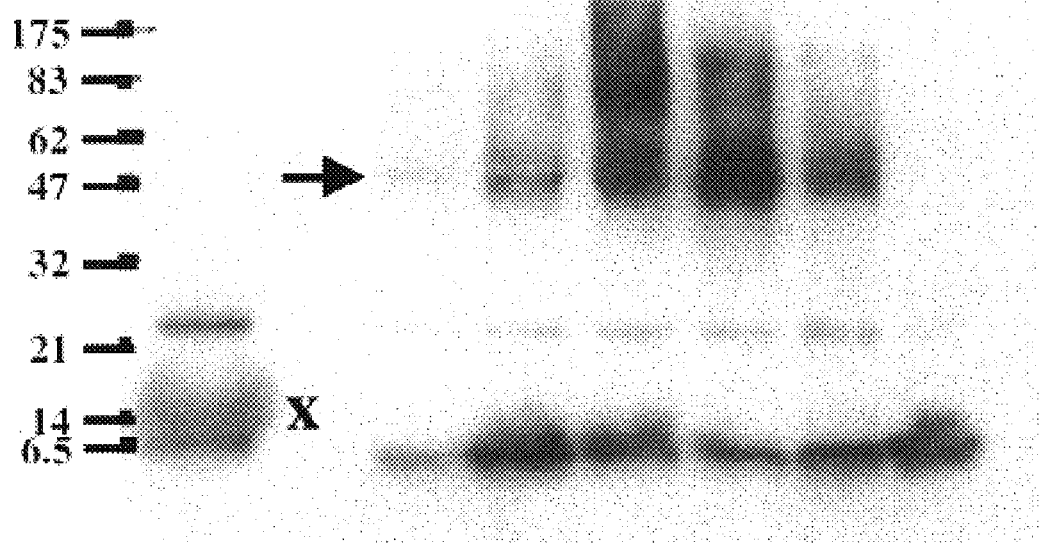
Figure 7:
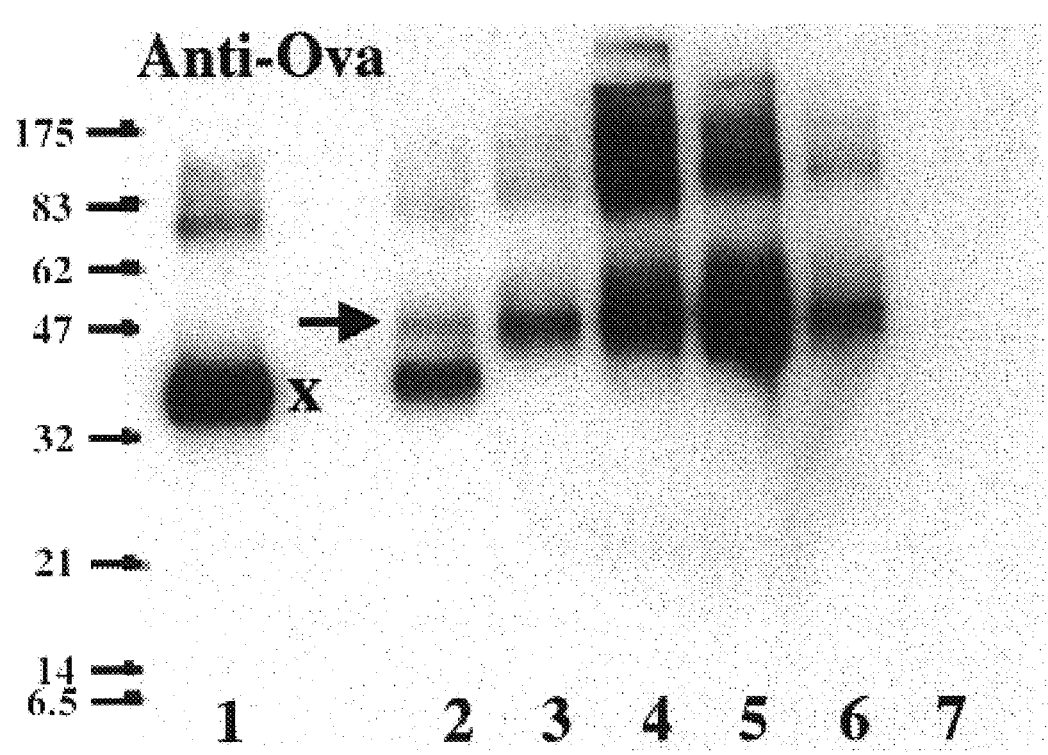

FIG. 7 shows western analysis of Ova coupling to STxB-Cys. The upper part of the figure represents an immunoblot using anti-STXB antibody, the lower part an immunoblot using anti-Ova antibody. The intermediates of different steps of the purification procedure are shown. Lane 1: uncoupled proteins (marked by a cross). Lane 2: coupling reaction (coupling product marked by an arrow). Lane 3: eluate of the immunoaffinity column doted with anti-STxB antibody. Lanes 4-7: fractions from the gelfiltration column. Lane 4: fractions 9-10. Lane 5: fractions 11-12. Lane 6: fractions 13-14. Lane 7: fractions 15-19 (free STxB-Cys). Fractions 11-12 contain the bulk of monomeric coupling product. Some material with lower electrophoretic mobility can also be detected, originating likely from dimeric Ova present in the original preparation.

Figure 8:
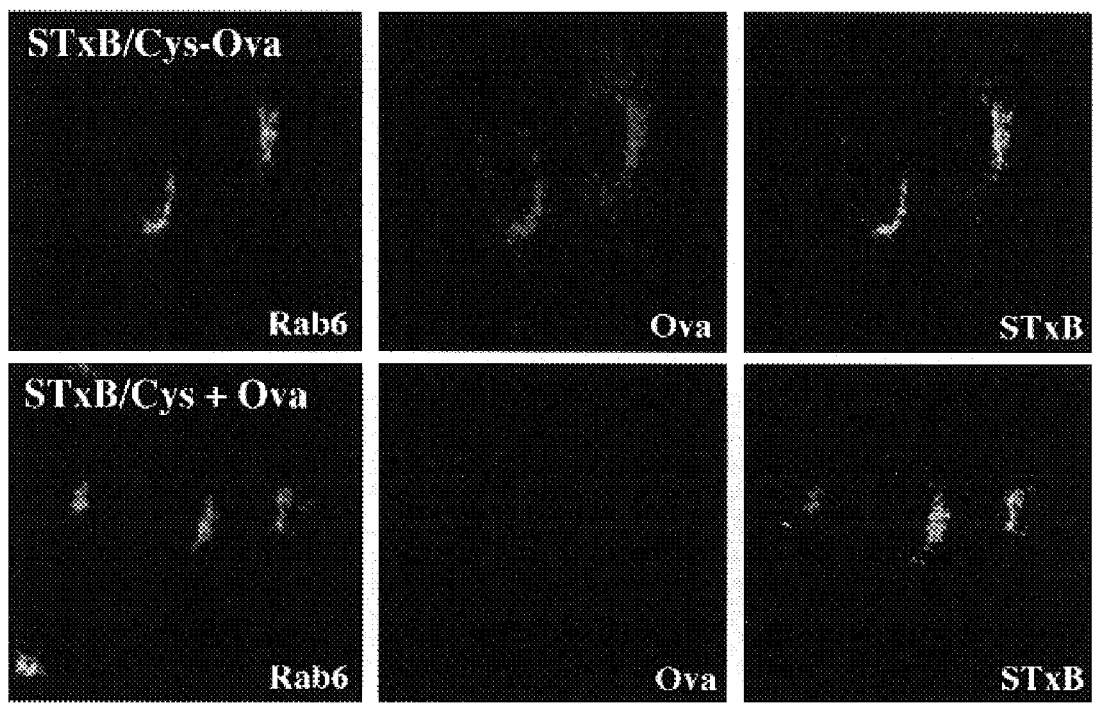

FIG. 8 represents immunofluorescence analysis of STxB-Cys-Ova transport in HeLa cells. The coupling product STxB-Cys-Ova (upper part of the figure) or a mixture of STxB-Cys and Ova (lower part of the figure) were incubated with HeLa cells on ice. After washing, the cells were shifted for 45 min to 37° C., fixed, and stained with the indicated antibodies. Note that when Ova is linked to STxB-Cys (top), the protein is vectorized into the Golgi apparatus, co-stained for the Golgi marker Rab6. If Ova is only mixed with STxB-Cys (bottom), the protein cannot be detected on the cells.

Figure 9B:
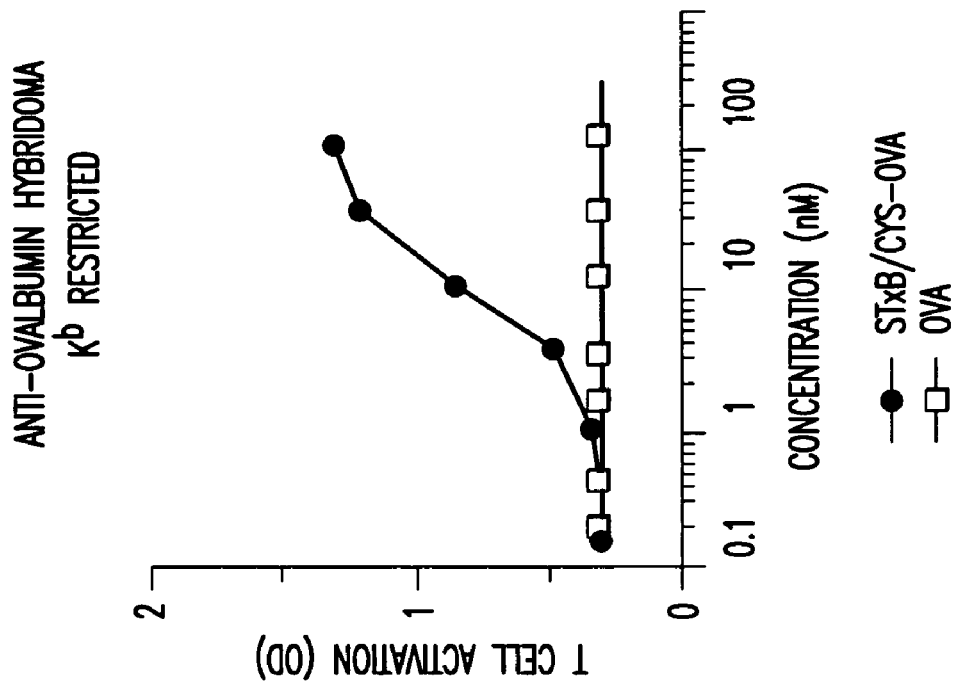
Figure 9A:
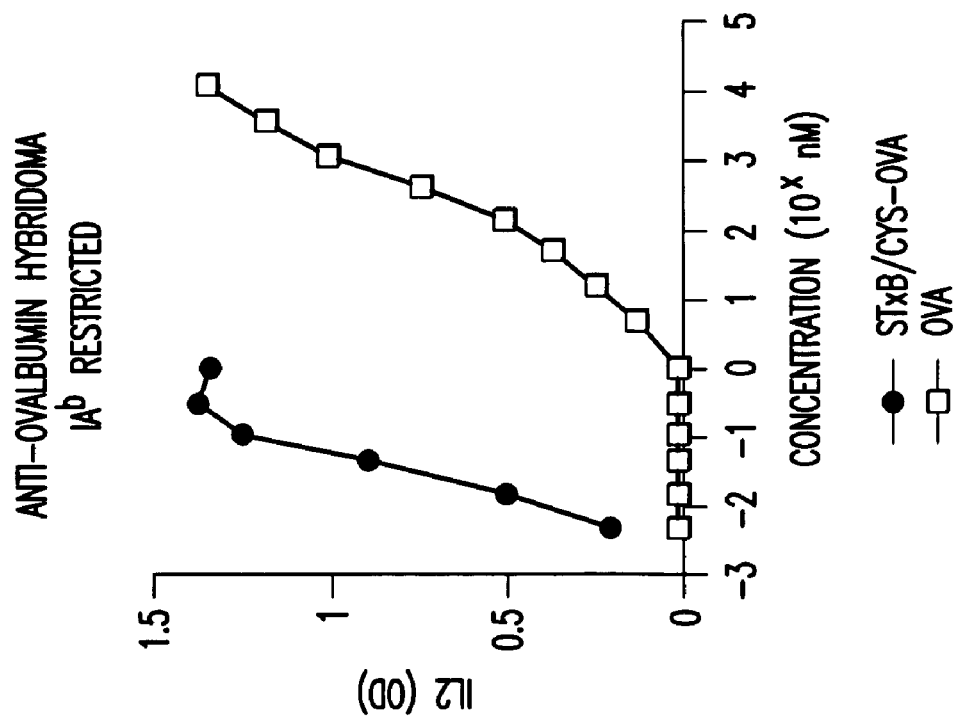

FIG. 9 shows MHC class I and II restricted antigen presentation induced by incubation of D1 cells with STxB-Cys-Ova. See text for details.

EXAMPLE 1

Figure 2A:
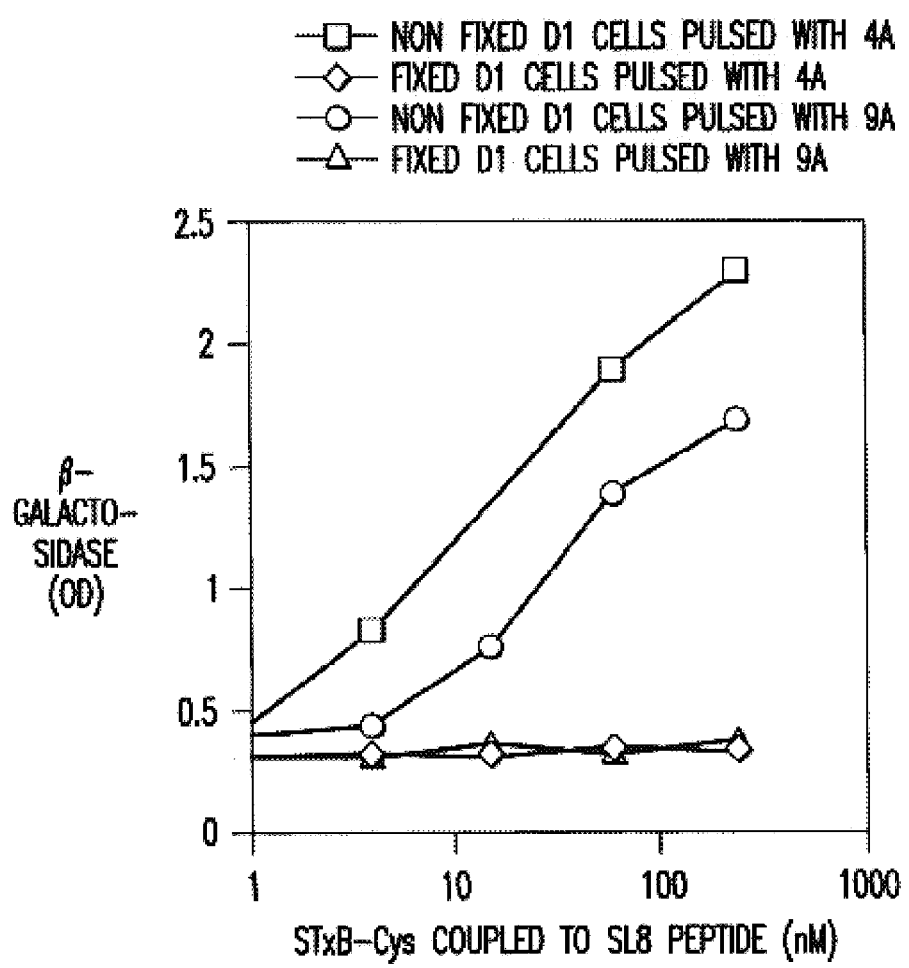

Preparation of the Universal Carrier a) Construction of a Plasmid Expressing STxB-Cys:

In a preferred embodiment, the plasmid pSU108 (7) was modified to introduce the Cysteine codon tgt at the 3' end of the B-fragment cDNA. PCR primer A: SEQ ID no 3 ID no 4 were used with plasmid specific primers ShigaAtpE: and Shiga-fd: to produce DNA fragments which, in a second PCR with primers Shiga AtpE and Shiga-fd yielded a fragment that was cloned into the SphI and SalI restriction sites of pSU108. Sequences derived by PCR were verified by dideoxy-sequencing.

```
(5'-AGCGAAGTTATTTTTCGTTGTTGACTCAGAATAGCTC-3')
and primer A': SEQ ID no 4
(5'-GAGCTATTCTGAGTCAACACGAAAAATAACTTC-3')
``` b) Protein Purification:

b) 1. Preparation of the Periplasmic Extract was Performed as Follows:

- Inoculate 125 ml of LB/Amp with 125 μl of an overnight culture grown at 30° C.,
- grow over night at 30° C.,
- transfer into 375 ml of LB/Amp at 50° C.; incubate 4 hours at 42° C.,
- centrifuge to pellet cells,
- wash cells 3 times with 10 mM Tris/HCl, pH 8.0,
- re-suspend cells in 200 ml of 25% sucrose, 1 mM EDTA, 10 mM Tris/HCl, Ph 8.0; incubate at room temperature for 10 min.,
- centrifuge to pellet cells,
- re-suspend cells in 200 ml of ice cold water containing a protease inhibitor cocktail; incubate on ice for 10 min.,
- centrifuge; collect supernatant; add 20 mM Tris/HCl, Ph8.0.

b) 2. Purification on Columns:

The periplasmic extract was loaded on a QFF anion exchanger column (pharmacia) and eluted at 230 mM Nacl. STxB-Cys containing fractions are pooled, diluted 4-fold and loaded on a Mono Q anion exchanger column (pharmacia), followed by elution at 230 mM Nacl. After concentration with microconcentration devices from PallFiltron, the pooled fractions were passed through a Sephadex 75 gel filtration column. Purity was above 95% (FIG. 1).

b) 3. Product Characterization:

The B-fragments of STxB-Cys, purified from Sephadex 75 gel filtration columns, are essentially monomeric (FIG. 1). This is in marked difference to constructions where the Cysteine was added at more than 2 amino acids from the natural C-terminus of the B-fragment. In these cases, neighbouring B-fragments within a pentamer are engaged in disulfide bonds.

EXAMPLE 2

Conditions for Coupling of Activated Peptides to the Universal Carrier a) Carriers:

Three different carriers have been compared.

1) STxB-Cys: B-fragment to which a Cys has been added right to its C-terminus. This protein elutes as a monomer from the purification columns.

2) STxB-$Z_2$-Cys: carrier with a short spacer (2 amino acids resulting from a cloning cassette) between the C-terminus of the wild type B-fragment and the Cys. The majority of the protein eluted as dimers from the purification columns. These can be separated under reducing conditions, indicating the formation of disulfide bonds between monomers in the pentameric B-subunit complex.

3) STxB-Glyc-Cys-KDEL: carrier in which the Cys is located between a Glycosylation cassette being 9 amino acid long and a C-terminal KDEL peptide. The majority of the protein eluted as dimers from the purification columns. These can be separated under reducing conditions, indicating the formation of disulfide bonds between monomers in the pentameric B-subunit complex.

b) Test Peptides:

1) Pep1: a synthetic peptide of 16 amino acids carrying the SL8 antigenic peptide derived from chicken ovalbumin.

2) Pep2: a synthetic peptide of 24 amino acids as above with, in addition, a His-gag at its C-terminus.

3) SL8: the antigenic peptide from ovalbumin that can directly exchange with peptides on MHC class I complexes at the plasma membrane of antigen presenting cells.

c) Coupling Conditions:

Under reducing conditions (Type1): Fusion proteins were treated with DTT overnight, then activated peptide (carrying a bromo acetate group at its N-terminus) was added in excess. Conditions used for the first coupling experiments using fusion proteins will mostly dimerize monomers (proteins STxB-$Z_2$-Cys and STxB-Glyc-Cys-KDEL).

Under non-reducing conditions (Type2): Fusion proteins are directly reacted with the activated peptides.

d) Biochemical and Morphological Controls:

Pep2 carries a His-tag. This has allowed us, using an anti-His antibody, to show the presence of Pep2 on B-subunit by Western blotting, and the B-subunit dependent transport of Pep2 in HeLa cells.

FIG. 2*a* shows that a dose dependent stimulation of the B3Z CTL hybridoma (measurement of β-galactosidase activity) was observed with non-fixed cells, while fixation abolished antigen presentation.

Note that antigen presentation only works on non-fixed cells, indicating that the observed presentation does not result from contaminating free Pep2.

FIG. 2b shows the control experiment of FIG. 2a in which it is shown that fixed D1 cells can still present free SL8 peptide.

Figure 3:
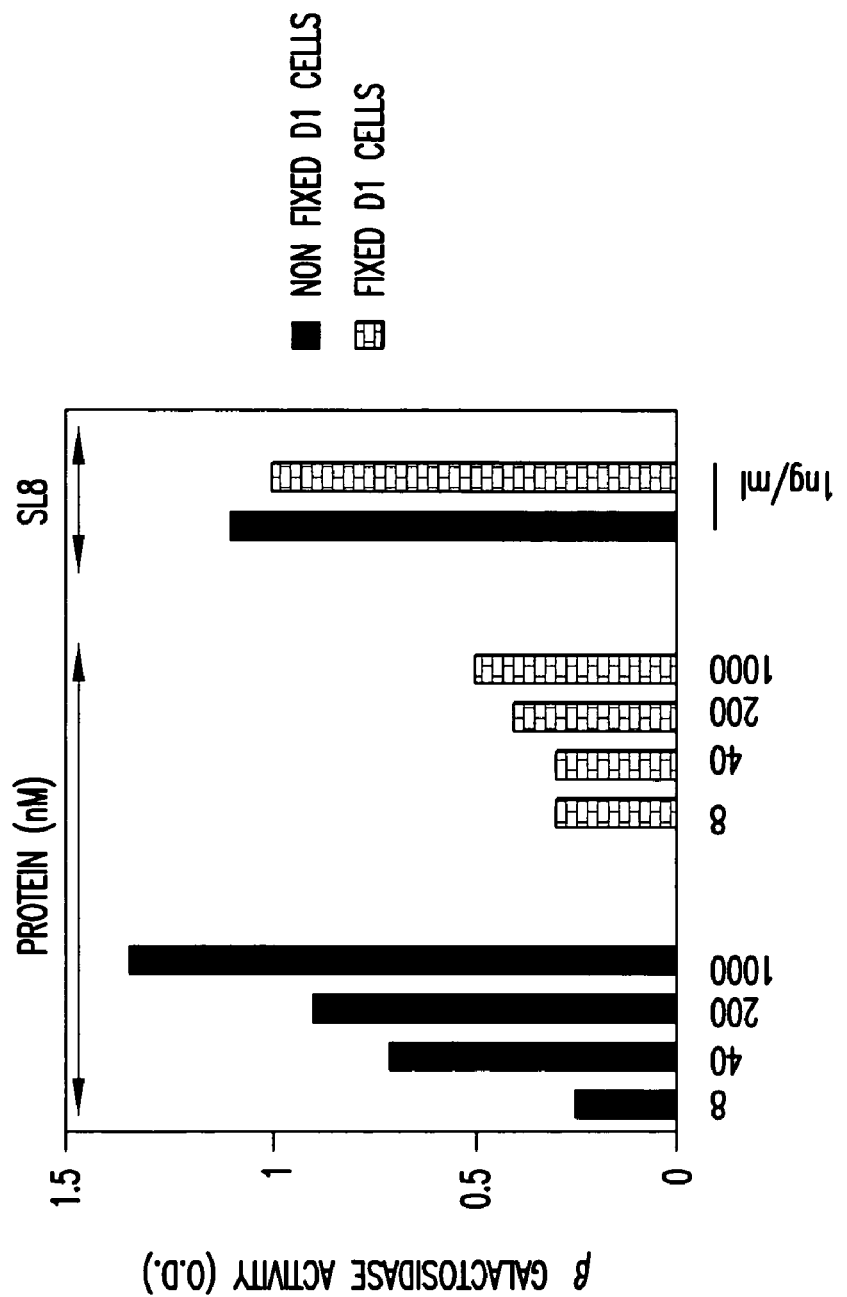
FIG. 3 represents another experiment on fixed and non fixed D1 cells using a coupling reaction of Type1 on STxB-SH and Pep1 [as defined in example 2].

In FIG. 3, it appears that in this type of protocol, some free Pep1 appears to co-purify with the fusion protein, since at high doses (200-1000 nM), some presentation was observed on fixed cells. Presentation by SL8 is shown to the right.

Figure 4:
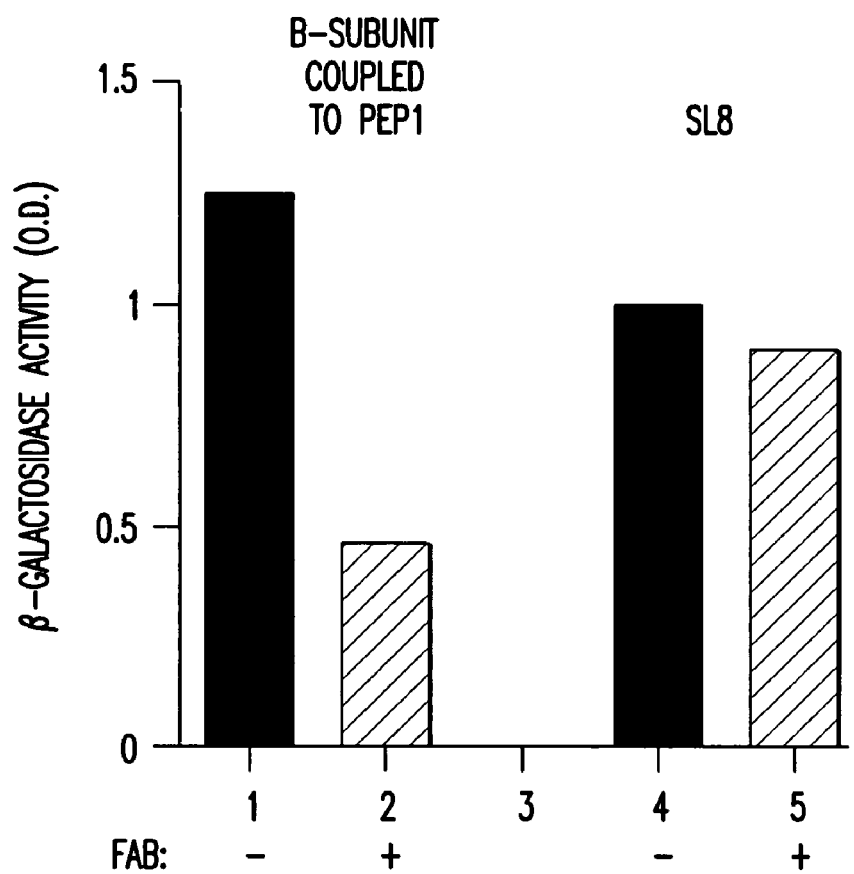
FIG. 4 represents the B-subunit dependent presentation of antigenic peptides derived from a coupling of Pep2 to B-Glyc-Cys-KDEL. The use of Fab fragments from an antibody that neutralizes STXB binding to Gb3 also abolishes antigen presentation.

In FIG. 4, the coupled protein (lanes 1 and 2) or the SL8 Peptide (lanes 5 and 6) were incubated (lanes 2 and 5) or not (lanes 1 and 4) with anti-B-subunit Fab-fragment derived from the 13C4 antibody which inhibits the binding of the B-subunit to Gb3. Note that the Fab-fragment neutralizes the capacity of the B-subunit to introduce the antigenic peptide into the class I pathway, while the presentation with SL8 is not affected under these conditions. The background signal in this experiment was at 0.3.

Figure 5A:
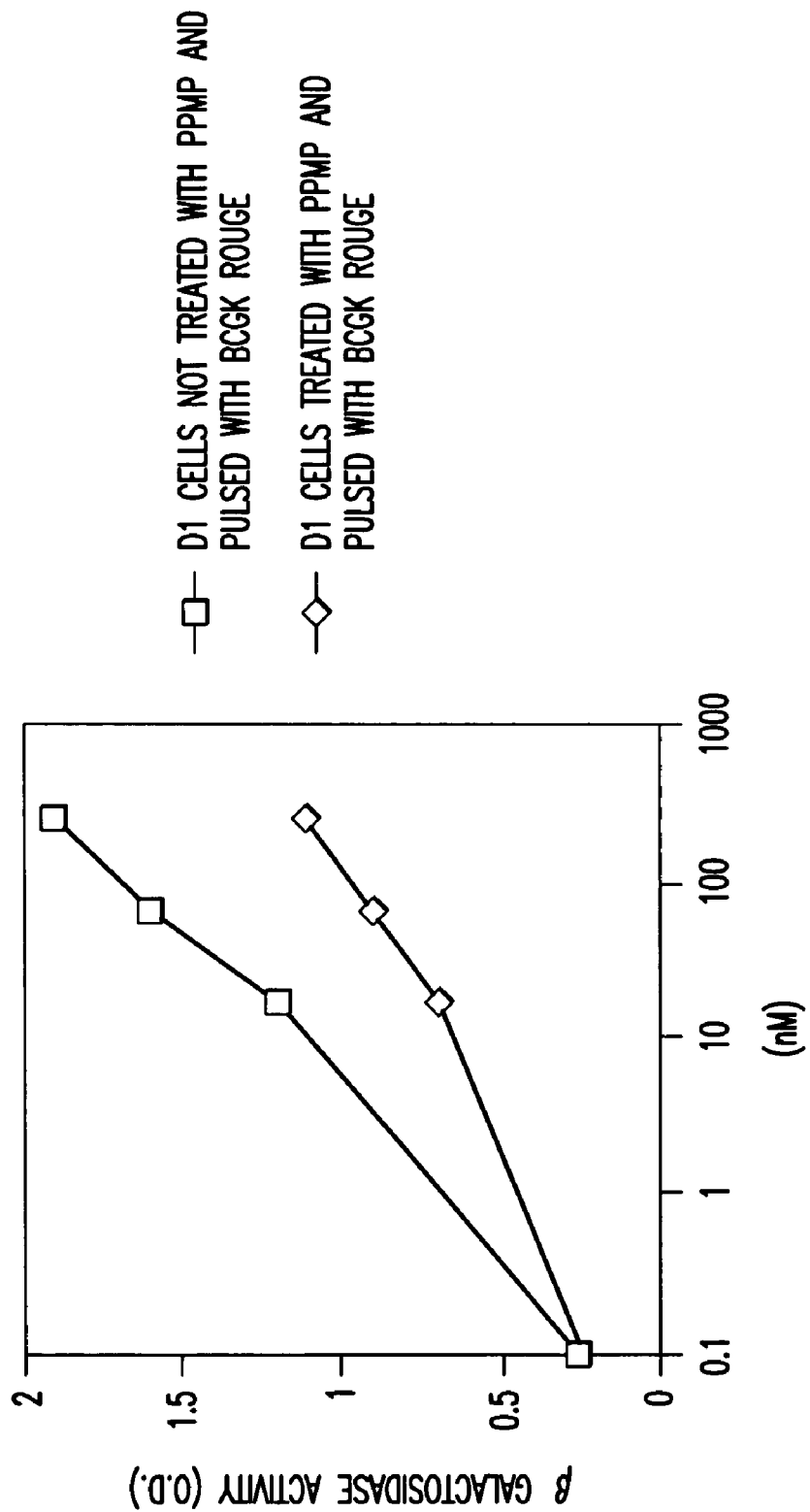
FIG. 5 shows that the Gb3 synthesis inhibitor PPMP inhibits B-subunit dependent antigen presentation (5*a*) and that SL8 presentation is not decreased in PPMP treated cells.
Figure 5B:
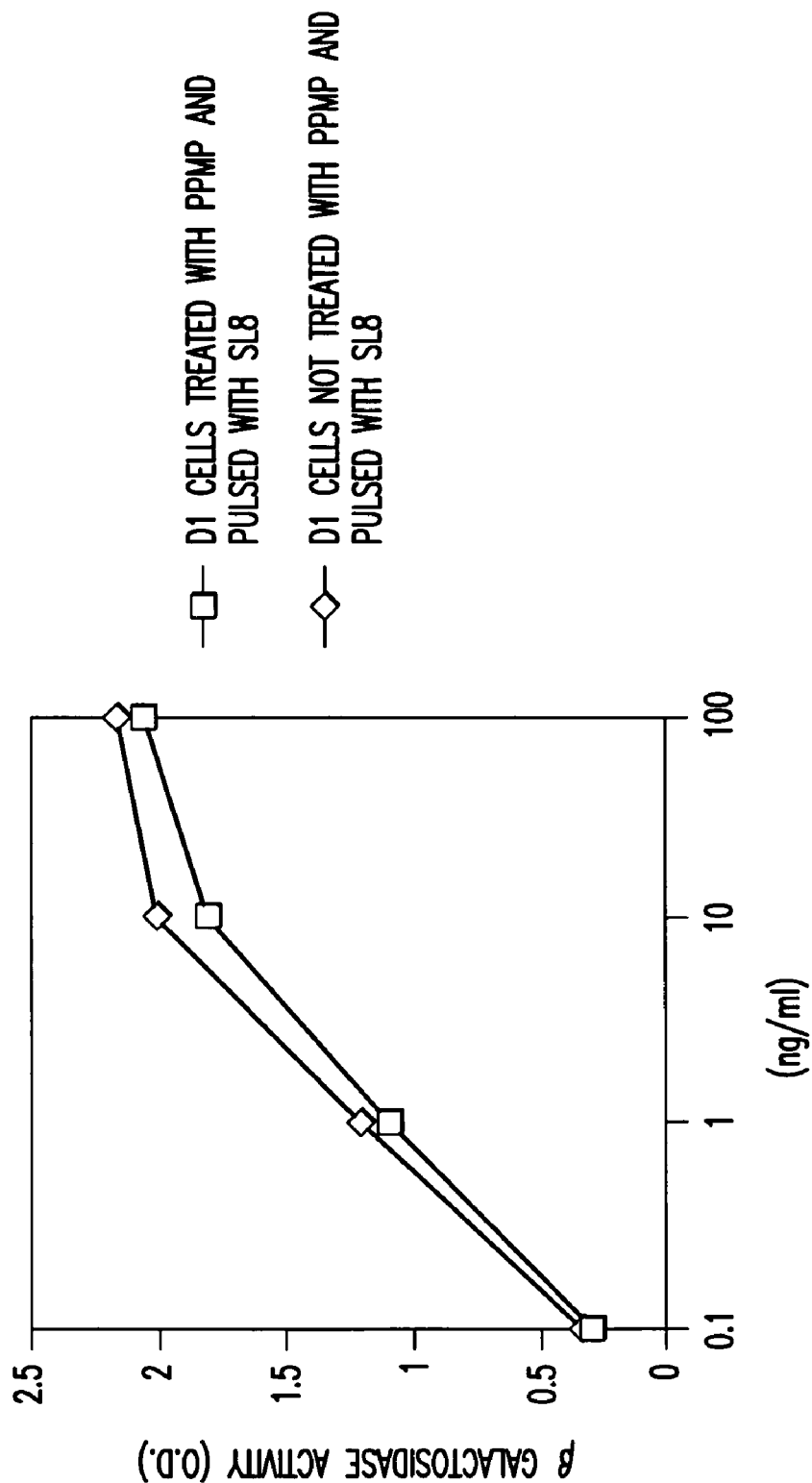

In FIG. 5a, $D_1$ cells were pre-treated with PPMP (see FIG. 3b of (2)) for 3 days. This treatment lead to an important decrease of Gb3 expression at the cell surface, without however eliminating it completely. Under this condition, antigen presentation from a coupling reaction of Pep1 with STxB-Glyc-Cys-KDEL was significantly reduced, indicating that Gb3 is important for the presentation phenomena.

Figure 1:
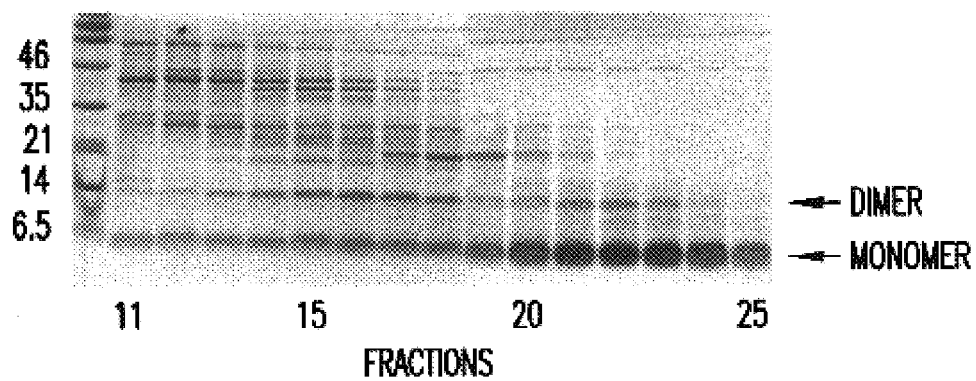

It appears from all these experiments that the coupling under non-reducing to STxB-Cys is surprisingly efficient (in terms of sensitivity; note that, as shown in FIG. 1, only 4 nM of STxB-Cys-Pep2 are necessary to have a response). Thus, the universal carrier STxB-Cys is preferred due to its simplicity in its preparation and to the reproducibility of the coupling.

Hence, the optimal conditions for coupling of activated peptides to STxB-Cys were the following:
dialyse STxB-Cys against 20 mM Borate buffer, pH 9.0, 150 mM NaCl,
concentrate to 1 mg/ml,
dissolve N-terminally activated peptide (activated with bromoacetate anhydride) at 12 mM in DMSO,
dilute peptide to 0.2 mM in protein solution,
incubate 12 hours at room temperature,
dialyse against PBS.

EXAMPLE 3

Characterization of STxB as to its Antigen Presentation Capacity

The following experimental series will help to fully describe the capacity of STxB to function in antigen presentation system.

a) Class I- and Class II-Restricted Antigen Presentation:

A peptide carrying class I- and II-restricted antigenic peptides from chicken ovalbumin (Br—CH2—CO—NH-LEQLESIINFEKLTEWSLKISQAVHAAHAEINEAGR (SEQ ID NO: 7), sequences 257-264 and 323-339 were coupled to STxB-Cys, and the class I- and class II-restricted presentation of these peptides were assayed using the corresponding T-cell hybridomas.

b) Coupling of Whole Size Proteins.

Our preliminary evidence suggests that chicken ovalbumin can be coupled to STxB-Cys. These experiments have been done with the SPDP heterobifunctional cross-linker. (Carlsson ≠et al., 1978).

A first series of antigen presentation experiments indicated that the ovalbumin protein can be introduced into the endogenous MHC class I-restricted antigen presentation pathway of mouse dendritic cells. SPDP has the inconvenience of being cleavable by serum thiolases. This cross-linker was successfully substituted by MBS which is non-cleavable. Other antigenic proteins (Mart 1 and polypeptides derived from HPV16-E7 and Muc1) are tested to show that the procedure is of universal use.

c) Coupling of Complex Protein Mixtures.

A lysate from the cervix carcinoma-derived cell line Caski is used. This cervix carcinoma cell line, which expresses the HLA-A2 allele at its membrane, also expresses Human papillomavirus derived peptides. E7 is a early transcribed ORF from HPV which is necessary for transformation of primary keratinocytes. Since anti-E7 HLA A2-restricted CTL are elicited in vitro. The efficacy of the coupling of this protein mixture by a presentation assay specific for HLA-A2 E7 derived peptides was tested. As control, a lysate from a HLA-A2-positive cell line which does not express E7 (croft cells or Daudi) was coupled to STxB-lys.

EXAMPLE 4

Application to MHC class I-restricted Antigen Presentation

The experiment of FIG. 4 shows that STxB-Cys dependent antigen presentation is inhibited when the interaction with $Gb_3$ is abolished. Here it is found that prebinding of the Fab fragment of monoclonal Ab against STxB to 0.1 μM STxB-Cys, coupled to SL8, inhibited antigen presentation, suggesting that STxB-Cys binding to $Gb_3$ is necessary for antigen presentation. Similar results were obtained when $Gb_3$-expression was inhibited with a drug (FIG. 4).

EXAMPLE 5

Reaction Chain for Coupling Ovalbumine to the STxB-Cys

The reaction scheme is shown in FIG. 6.

In a first reaction, the N-hydroxysuccinimide ester moiety of MBS reacts with primary amines on an antigenic target protein, such as the model protein ovalbumin (Ova). The reaction product is purified and then incubated in a second reaction with STxB-Cys leading to coupling via the maleimidobenzoyl moiety.

FIG. 7 shows the SDS-PAGE and Western analysis of a typical coupling reaction involving STxB-Cys and Ova. For coupling, 20 mg/ml of Ova in 100 mM HEPES, pH 7.4, was incubated with 4.5 mM of MBS for 30 min at room temperature. The reaction is passed through a PBS/EDTA 10 mM equilibrated gel filtration column. Eluted Ova is concentrated to 20 mg/ml. 1 volume of STxB-Cys at 3.5 mg/ml in PBS/EDTA is mixed with 1 volume of activated Ova and incubated over night at room temperature.

FIG. 7 shows that within the coupling reaction, bands with lower electrophoretic mobility (labeled with arrows; coupling product) can be detected in addition to uncoupled STxB (upper part) and uncoupled Ova (lower part; uncoupled proteins are labeled with a cross). The reaction product is purified by passage through an immunoaffinity column made with 13C4 anti-STxB monoclonal antibody (lane IP column). Note that free Ova is eliminated. Eluted STxB-Cys (coupled and non-coupled) is then passed through a gel filtration column to separate free STXB (fractions 15-19) from coupled STxB-Cys (fractions 9-14; note that fractions 11-12 contain the bulk of coupled protein; the upper coupling band, which is minor compared to the lower band, probably results from dimeric Ova).

EXAMPLE 6

Intracellular Transport Characteristics of STxB-Cys-Ova Coupling Product 0.5 µM of STxB-Cys-Ova was incubated with HeLa cells on ice. The cells were washed and shifted to 37° C. for 45 min, fixed, and stained for the indicated antibodies. As shown in FIG. 8, when STxB-Cys and Ova were linked by MBS, Ova immunoreactivity could be detected together with STxB immunoreactivity in the Golgi apparatus, stained by Rab6. When both proteins are incubated as separate entities with HeLa cells, only STxB-Cys is transported to the Golgi, while Ova cannot be detected on the cells. These data clearly show that couples STxB-Cys is still transported in the same manner as uncoupled STxB-Cys, and that Ova is vectorized via STxB-Cys.

EXAMPLE 7

The STxB-Cys Allows Both, MHC Class I and II Restricted Presentation of Peptides Derived from Full Size Exogenous Antigenic Proteins In a first experiment (FIG. 9, left), we have shown that when STxB-Cys-Ova is used to sensitize the murine dendritic cell line D1, a clear increase of the presentation of the MHC class II restricted Ova derived peptide $Ova_{323-339}$ is observed, compared to D1 cells pulsed with non-vectorized Ova. Indeed, a significant presentation of $Ova_{323-339}$ peptide could be detected with as little as 0.01 nM of STxB-Cys-Ova, whereas 10 nM of full size Ova was required for an efficient presentation of the same peptide. The presentation of the $IA^b$ restricted $Ova_{323-339}$ peptide was revealed using the B097.10 hybridoma that produces IL-2 after recognition of this peptide. As a control, we did not observe IL-2 secretion when an irrelevant MHC class II restricted hybridoma was used instead of B097.10 (data not shown).

In a second experiment, we have pulsed the same D1 dendritic $H2^b$ restricted cell line with either Ova alone or with STxB-Cys-Ova. No presentation of the Ova-derived immunodominant SL8 peptide ($Ova_{257-264}$) was observed when the D1 cells were sensitized with up to 100 nM of free Ova, while 1-10 nM of STxB-Cys-Ova allowed the presentation of the SL8 peptide, as revealed by the specific B3Z hybridoma that recognize the SL8 peptide in the context of $K^b$ molecules. As a control, it was shown that no activation of an irrelevant hybridoma was observed under the same experimental conditions.

Altogether, these results clearly demonstrate that STxB-Cys targets full size proteins with high efficiency into both, the MHC class I and class II pathways.

BIBLIOGRAPHY (1) Ren-Shiang Lee, Eric Tartour, Pierre van der Bruggen, Valerie Vantomme, Isabelle Joyeux, Bruno Goud, Wolf Herman Fridman and Ludger Johannes, "Major histocompatibility complex class I Presentation of exogenous soluble tumor antigen fused to the B-fragment of Shiga toxin". Eur. J. Immunol. (1998) 28: 2726-2737.

(2) Nacilla Haicheur, Emmanuelle Bismuth, Sophie Bosset, Olivier Adotevi, Guy Warnier, Valérie Lacabanne, Armelle Regnault, Catherine Desaymard, Sebastian Amigorena, Paola Ricciardi-Castagnoli, Bruno Goud, Wolf H. Fridman, Ludger Johannes and Eric Tartour, "The B Subunit of Shiga Toxin Fused to a Tumor Antigen Elicits CTL and Targets Dendritic Cells to Allow MHC Class I-Restricted Presentation of Peptides Derived from Exogenous Antigens". The Journal of Immunology (2000) 165: 3301-3308.

(3) Noakes, K. L., H. T. Teisseranc, J. M. Lord, P. R. Dunbar, V. Cerundolo and L. M. Roberts "Exploiting retrograde transport of Shiga-like toxin 1 for the delivery of exogenous antigens into the MHC class I presentation pathway". Febs. Lett. (1999) 453:95.

(4) Philippe Schelté, Christophe Boeckler, Benoît Frisch and Francis Schuber "Differential Reactivity of Maleimide and Bromoacetyl functions with Thiols: Application to the Preparation of Liposomal Diepitope Constructs". Eur. J. Immunol. (1999) 29:2297-2308.

(5) Carlsson, J., H. Drevin, and R. Axen. 1978. Protein thiolation and reversible protein-protein conjugation. N-Succinimidyl 3-(2-pyridyldithio)propionate, a new heterobifunctional reagent. *Biochem. J.* 173:723-737.

(6) Su, G. F., H. N. Brahmbhatt, J. Wehland, M. Rohde and K. N. Timmis "Construction of stable LamB-Shiga toxin B subunit hybrids: analysis of expression in *Salmonella typhimurium* aroA strains and stimulation of B subunit-specific mucosal and serum antibody responses". (1992) Infect. Immun. 60:3345-3359.

(7) Johannes, L., Tenza, D., Antony, C. and Goud, B., "Retrograde transport of KDEL-bearing B-fragment of Shiga toxin". (1997) J. Biol. Chem. 272: 19554-19561.

(8) N. A. Stockbine, M. P. Jackson, L. M. Sung, R. K. Holmes, A. D. O'Brien, J Bacteriol 170, 1116-22 (1988).

---

The invention claimed is:

1. A universal polypeptidic carrier for targeting directly or indirectly a molecule to Gb3 receptor expressing cells and having the following formula STxB-Z(n)-Cys, wherein:
   STxB is the Shiga Toxin B subunit or a functional equivalent thereof,
   Z is an amino-acid devoid of a sulfhydryl group, n being 0, 1 or a polypeptide,
   Cys is the amino-acid Cysteine, wherein said molecule is an antigen to be targeted to antigen presenting cells.

2. The universal carrier according to claim 1 wherein n is 0.

3. The universal carrier according to claim 1 or 2 wherein the molecule is covalently linked to the —S residue of the universal carrier by a —S—S—, a —S—CO—, a —S—CH$_2$— or a —S—NH— linkage.

4. The universal carrier according to claim 1 or 2 wherein the universal carrier is covalently linked to an oligopeptide or a polypeptide by a —S—S—, or a —S—CO—, or a —S—CH$_2$— or a —S—NH— linkage, and the molecule to be targeted is operably linked to said oligopeptide or polypeptide.

5. The universal carrier according to claim 4 wherein the universal carrier is covalently linked to a poly-lysine oligopeptide and the molecule to be targeted is nucleic acid or an oligo-nucleotide operably linked to the said poly-lysine moiety.

6. The universal carrier according to claim 3 wherein the molecule is a cytotoxic drug or a pro-drug to be targeted to tumor cells expressing Gb3 receptors.

7. A universal carrier for targeting directly or indirectly a molecule to Gb3 receptor expressing cells and having the following formula STxB-Z(n)-Cys, wherein:
   STxB is the Shiga Toxin B subunit or a functional equivalent thereof,
   Z is an amino acid devoid of a sulfhydryl group, n being 0, 1 or a polypeptide,
   Cys is the amino acid Cysteine, wherein said molecule is selected from the group of proteins, glycoproteins, nucleic acids encoding proteins and a combination thereof.

8. A universal polypeptidic carrier for targeting directly or indirectly a molecule to Gb3 receptor expressing cells and having the following formula STxB-Z(n)-Cys, wherein:
   STxB is the Shiga Toxin B subunit,
   Z is an amino acid devoid of a sulfhydryl group, n being 0, 1 or a polypeptide,
   Cys is the amino acid Cysteine, wherein said molecule is selected from the group of proteins, glycoproteins, nucleic acids encoding proteins and a combination thereof.

9. A universal polypeptidic carrier for targeting directly or indirectly a molecule to Gb3 receptor expressing cells and having the following sequence:

(SEQ ID No; 1)
COOH-
MKKTLLIAASLSFFSASALATPDCVTGKVEYTKYNDDDTFTVKVGDKELF
TNRWNLQSLLLSAQITGMTVTIKTNACHNGGGFSEVIFRC-NH$_2$.

10. A universal polypeptidic carrier for targeting directly or indirectly a molecule to Gb3 receptor expressing cells and having the following formula STxB-Z(n)-Cys, wherein:
   STxB is the Shiga Toxin B subunit,
   Z is an amino acid devoid of a sulfhydryl group, n being 0, 1 or a polypeptide,
   Cys is the amino acid Cysteine, wherein said molecule is a cytotoxic drug or a pro-drug to be targeted to tumor cells expressing Gb3 receptors.

11. A universal polypeptidic carrier for targeting directly or indirectly a molecule to Gb3 receptor expressing cells and having the following formula STxB-Z(n)-Cys, wherein:
  STxB is the Shiga Toxin B subunit or a functional equivalent thereof,
  Z is an amino-acid devoid of a sulfhydryl group, n being 0, 1 or a polypeptide,
  Cys is the amino-acid Cysteine, wherein the molecule is selected from the group consisting of proteins, peptides, oligopeptides, glycoproteins, glycopeptides, nucleic acids, polynucleotides, and a combination thereof.

* * * * *